(12) United States Patent
Theodotou

(10) Patent No.: US 11,234,943 B2
(45) Date of Patent: Feb. 1, 2022

(54) USE OF RESERVATROL FOR THE TREATMENT OF NON-ALCOHOLIC FATTY LIVER DISEASE (NAFLD)

(71) Applicant: Marios Andreou Theodotou, Limassol (CY)

(72) Inventor: Marios Andreou Theodotou, Limassol (CY)

( * ) Notice: Subject to any disclaimer, the term of this patent is extended or adjusted under 35 U.S.C. 154(b) by 66 days.

(21) Appl. No.: 16/327,708

(22) PCT Filed: Aug. 25, 2017

(86) PCT No.: PCT/IB2017/055126
§ 371 (c)(1),
(2) Date: Feb. 22, 2019

(87) PCT Pub. No.: WO2018/037382
PCT Pub. Date: Mar. 1, 2018

(65) Prior Publication Data
US 2019/0209488 A1    Jul. 11, 2019

(30) Foreign Application Priority Data
Aug. 26, 2016 (EP) ..................... 16186058

(51) Int. Cl.
*A61K 31/05* (2006.01)
*A61P 1/16* (2006.01)
*A61K 9/50* (2006.01)

(52) U.S. Cl.
CPC ............... *A61K 31/05* (2013.01); *A61K 9/50* (2013.01); *A61P 1/16* (2018.01)

(58) Field of Classification Search
CPC .................................. A61K 31/05; A61P 1/16
See application file for complete search history.

(56) References Cited

U.S. PATENT DOCUMENTS

| | | | |
|---|---|---|---|
| 2011/0092529 A1* | 4/2011 | Brown | C07D 491/10 514/278 |
| 2013/0281309 A1* | 10/2013 | Meno | C07K 14/8114 506/9 |
| 2014/0363526 A1* | 12/2014 | Chitre | A61K 36/47 424/725 |

FOREIGN PATENT DOCUMENTS

| | | | |
|---|---|---|---|
| CN | 105267187 | * | 1/2016 |
| WO | WO 2010/100197 | * | 9/2010 |
| WO | WO-2010100197 A1 | | 9/2010 |
| WO | WO-2018037382 A1 | | 3/2018 |

OTHER PUBLICATIONS

Faghihzadeh et. al (Nutrition Research (2014) 837-843). (Year: 2014).*
Gomez-Zorita et. al. (British Journal of Nutrition (2012) 107:202-210). (Year: 2012).*
Andrade et. al. (Nutrition (2014) 30:915-919). (Year: 2014).*
Reagan-Shaw et. al. (FASEB Journal (2007) 22:659-661). (Year: 2007).*
Chen et. al. (Digestive and Liver Disease (2015) 47:226-232). (Year: 2015).*
Chachay (Clinical Gastroenterology and Hepatology (2014) 12:2092-2103) (Year: 2014).*
Heeboll et. al. (Scandinavian Journal of Gastroenterology (2016) 51:456-463). (Year: 2016).*
"European Application No. 16186058.0, Extended European Search Report dated Jan. 12, 2017", (Jan. 12, 2017), 3 pgs.
"International Application No. PCT/IB2017/055126, International Search Report and Written Opinion dated Nov. 3, 2017", (Nov. 3, 2017), 15 pgs.
Ali, Mahmoud Hussein Hassan, et al., "Protective effect of ursodeoxycholic acid, resveratrol, and N-acetylcysteine on nonalcoholic fatty liver disease in rats", Pharmaceutical Biology, 54:7, (Jul. 1, 2015), 1198-1208.
Chen, Shihui, et al., "Resveratrol improves insulin resistance, glucose and lipid metabolism in patients with non-alcoholic fatty liver disease: A randomized controled trial", Digestive and Liver Disease, vol. 47, No. 3, (Dec. 16, 2014), 226-232.
Faghihzadeh, Forouzan, et al., "Resveratrol supplementation improves inflammatory biomarkers in patients with nonalcoholic fatty liver disease", Nutrition Research, vol. 34, No. 10, (Sep. 23, 2014), 837-843.
Gomez-Zorita, S., et al., "Resveratrol attenuates steatosis in obese Zucker rats by decreasing fatty acid availability and reducing oxidative stress", British Journal of Nutrition (2012), vol. 107, No. 2, (Jun. 28, 2011), 202-210.
Heeboll, Sara, et al., "Placebo-controlled, randomised clinical trial: high-dose resveratrol treatment for non-alcoholic fatty liver disease", retrieved from internet on Jan. 5, 2017: URL:http://www.tandfonline.com/doi/full/10.3109/00365521.2015.1107620?scroll=top&needAccess=true, (Jan. 5, 2017), 9 pgs.
Howells, Lynne M., et al., "Phase I Randomized, Double-Blind Pilot Study of Micronized Resveratrol (SRT501) in Patients with Hepatic Metastases—Safety, Pharmacokinetics, and Pharmacodynamics", Cancer Prevention Research, vol. 4, No. 9, (Jun. 16, 2011), 1419-1425.

(Continued)

*Primary Examiner* — Marcos L Sznaidman
(74) *Attorney, Agent, or Firm* — Schwegman Lundberg & Woessner, P.A.

(57) ABSTRACT

Micronized trans-resveratrol is provided in 50-200 mg unit dosage form for use as a single unit dose daily for administration to human patients the treatment or prevention of non-alcoholic fatty liver disease and/or for the treatment, prevention or reversal of non-alcoholic hepatic steatosis, e.g. for administration to patients exhibiting evidence of fatty liver on ultrasonography. A reported study shows the effects of resveratrol micronized formulation in reducing the liver fat, decreasing hepatic enzymes, serum glutamate pyruvic transaminase (SGPT) and gamma-glutamyl transpeptidase (g-GT) and decreasing insulin resistance. At the end of the study, statistical analysis showed a strongly statistically significant reduction in the liver fat, which in some patients continued for an extended period after treatment was discontinued. These results demonstrate that use of resveratrol in micronized formulation improves features of NAFLD, prevents liver damage and that resveratrol micronized formulation can be an effective treatment for NAFLD.

5 Claims, No Drawings

(56) References Cited

OTHER PUBLICATIONS

Oliveira Andrade, Joao Marcus, et al., "Resveratrol attenuates hepatic steatosis in high-fat fed mice by decreasing lipogenesis and inflammation", Nutrition, vol. 30, No. 7, (2014), 915-919.

Reagan-Shaw, Shannon, et al., "Dose translation from animal to human studies revisited", The FASEB Journal, Federation of American Societies for Experimental Biology, vol. 22, (Jan. 1, 2007), 659-661.

Wicklow, Brandy, et al., "Proposed trial: safety and efficacy of resveratrol for the treatment of non-alcoholic fatty liver disease (NAFLD) and associated insulin resistance in adolescents who are overweight or obese adolescents—rationale and protocol", Biochemistry and Cell Biology, vol. 93, No. 5, (Oct. 2015), 522-530.

Zhang, Chongyang, et al., "Efficacy of Resveratrol Supplementation Against Non-Alcoholic Fatty Liver Disease: A Meta-Analysis of Placebo-Controlled Clinical Trials", PLoS ONE 11(8), (Aug. 25, 2016), 12 pgs.

International Application No. PCT/IB2017/055126, International Preliminary Report on Patentability dated Feb. 26, 2019, 11 pgs.

\* cited by examiner

USE OF RESERVATROL FOR THE TREATMENT OF NON-ALCOHOLIC FATTY LIVER DISEASE (NAFLD)

PRIORITY CLAIM TO RELATED APPLICATIONS

This application is a U.S. national stage filing under 35 U.S.C. § 371 from International Application No. PCT/IB2017/055126, filed on 25 Aug. 2017, and published as WO2018/037382 on 1 Mar. 2018, which claims the benefit under 35 U.S.C. 119 to European Patent Application No. 16186058.0, filed on 26 Aug. 2016, the benefit of priority of each of which is claimed herein, and which applications and publication are hereby incorporated herein by reference in their entirety.

FIELD OF THE INVENTION

The present invention relates to a method for treating non-alcoholic patients with fatty liver disease (NAFLD).

BACKGROUND OF THE INVENTION

According to statistics NAFLD affects up to 30% of people in Western continents (USA and EU) and 15% in Asian countries and also an increasing number of children (Vernon G, Baranova A, Younossi Z M: Systematic review: the epidemiology and natural history of non-alcoholic fatty liver disease and non-alcoholic slealohepatitis in adults. Aliment Pharmacol Ther 34: 274-285, 2011).

NAFLD is a clinical syndrome characterized by the accumulation of excess fat in the liver. It spans a spectrum of disease from pathological accumulation of triglyceride (TG)—steatosis to an inflammatory response—non-alcoholic steatohepatitis (NASH) (Chalasani N, Younossi 7, Lavine J E et al: The diagnosis and management of non-alcoholic fatty liver disease: practice guideline by the American Association for the Study of Liver Diseases, American College of Gastroenterology, and the American Gastroenterological Association, Hepatology 55:2005-2023, 2012). NASH may progress to cirrhosis, cirrhosis complications, liver failure and an increased risk of liver cancer. NAFLD is the third cause of liver transplantation in the United States (Charlton M R, Burns J M, Pedersen R A, Watt K D, Heimbach J K, Dierkhising R A: Frequency and outcomes of liver transplantation for non-alcoholic steatohepatitis in the United States, Gastroenterology 141:1249-1253, 2011). NAFLD is becoming a major health issue worldwide not only for its prevalence but also for its metabolic complications. The underlying insulin resistance is associated with hypertension, hyperlipidaemia, cardiovascular disease, type 2 diabetes mellitus (T2DM), chronic kidney disease and recently with carotid atherosclerosis (Bonora E, Targher G: Increased risk of cardiovascular disease and chronic kidney disease in NAFLD, Nat Rev Gastroenterol Hepatol 9:372-381, 2012; Angulo P: Nonalcoholic fatty liver disease, N Engl J Med 346:1221-31, 2002), Fracanzani A L, Burdick L, Raselli S, Pcdotti P, Grigorc L, Santorelli G, Valenti L, Maraschi A, Catapano A, Fargion S: Carotid artery intima-media thickness in non-alcoholic fatty liver disease, Am J Med: 121(1):72-8, 2008). Therapeutic options are limited, there is no pharmacological therapy and managing NAFLD focuses on the treatment of risk factors.

During the last decades, the potential of RSV has been explored. It has pleiotropic affects in various tissues. RSV is an activator of adenosine monophosphate-activated kinase (ANIPK) and silent information regulation 2 homolog 1 (SIRT1). These two proteins have a critical role in aiding fat breakdown and removal from the liver, associated with liver diseases such as fibrosis and cirrhosis (Kopec K L, Burns D: Non-alcoholic fatty liver disease: a review of the spectrum of disease, diagnosis, and therapy, Nutr Clin Pract 26:565-576, 2011). Through the activation of AMPK and SIRT1 in hepatic cells and anti-30 oxidant and anti-inflammatory actions, RSV may prevent liver damage and may inhibit the progression of NAFLD (Lagouge M, Argmann C, Gerhart-Hines Z. et al: Resveratrol improves mitochondrial function and protects against metabolic disease by activating SIRT1 and PGC-, Cell 127:1109-1122, 2006; Gomez-Zorita S, Fernandez-Quintela Macarulla M et al: Resveratrol attenuates steatosis in obese Zucker rats by decreasing fatty acid availability and reducing oxidative stress, Br J Nutr 107: 202-10, 2012).

A study by Chen S. et al., Resveratrol improves insulin resistance, glucose and lipid metabolism in patients with non-alcoholic fatty liver disease: a randomized controlled trial, Dig. Liver Dis., 2015 March; 47(3):226-32 aimed to evaluate the effect of resveratrol on insulin resistance, glucose and lipid metabolism in non-alcoholic fatty liver disease. In a double-blind randomized, placebo-controlled trial 60 subjects with non-alcoholic fatty liver disease were given two placebo capsules (placebo group) or two 150 mg resveratrol capsules (resveratrol group) twice daily for three months. Liver ultrasound imaging, anthropometric profile, serum liver enzymes, insulin, glucose, C-peptide, lipid profile, and inflammation-related cytokines were compared pre- and post-treatment. Compared with the placebo group, resveratrol significantly decreased aspartate aminotransferase, glucose and low-density lipoprotein cholesterol, alanine aminotransferase, total cholesterol and homeostasis model assessment insulin resistance index. In the resveratrol group significant reductions of the levels of TNF-$\alpha$, cytokeratin 18 fragment, and fibroblast growth factor and elevation of adiponectin level were observed. However, side-effects from intake of relatively high intakes of resveratrol have been reported in some studies.

The value of resveratrol for the treatment of NALFD has not, however, been unequivocally accepted. Chongyang Zhang et al., Efficacy of Resveratrol Supplementation against Non-Alcoholic Fatty Liver Disease: A Meta-Analysis of Placebo-Controlled Clinical Trials, PLos ONE 11(8): e0161792 was based on a systematic search in EMBASE, PubMed, Science Citation Index, Elsevier, and Cochrane Library databases for relevant studies and either a fixed-effect model or random model was used to estimate mean difference (MD) and 95% confidence intervals (CIs) for the effect of resveratrol on NAFLD. Four randomized, double-blinded, placebo-controlled trials involving 156 patients were included in the meta-analysis, other studies being excluded because they were not clinical trials or had no available data. In addition to the Chen et al. study where as previously stated 150 mg capsules were taken twice daily, the Faghihzadeh et al. study administered a 500 mg capsule daily, the Heeball et al. study administered 500 mg three times daily and the Catchay et al. study administered 3000 mg daily. Levels of low-density lipoprotein (MD=0.47, 95% CI: 0.21, 0.74, P<0.05) and total cholesterol (MD=0.49, 95% CI: 0.18, 0.80, P<0.05) were higher in the resveratrol treatment groups than in placebo control groups, whereas other parameters were not altered. Overall, this study indicated that resveratrol treatment had negligible effects on attenuating NAFLD, given the small improvement in NAFLD features.

SUMMARY OF THE INVENTION

The present invention provides a method of reducing the fat on the liver with the use of resveratrol micronized formulation in humans with Non-Alcoholic Fatty Liver Disease (NAFLD) which is an increasing clinical problem for which effective treatments are required. Resveratrol is used in the form of micronized formulation (micronized trans-resveratrol formulation is better absorbed and is more effective than plain resveratrol formulations), which has strong antioxidant effects and is circulated at the market as a food supplement.

The invention provides micronized trans-resveratrol in 50-200 mg unit dosage form for use as a single unit dose daily for administration to human patients the treatment or prevention of non-alcoholic fatty liver disease. The resveratrol is suitable for administration to patients selected on the basis of exhibiting evidence of fatty liver on ultrasonography.

The invention further provides micronized trans-resveratrol in 50-200 mg unit dosage form for use as a single unit dose daily for administration to human patients for the prevention, treatment or reversal of non-alcoholic hepatic steatosis. It has been found that after administration of the transveratrol for a period of some months e.g. up to 6 months, reversal of steatosis may be achieved in some human patients evidenced e.g. by the difference in sonographic signals between the liver and the right kidney, and that the reversal may be maintained or may even be progressive for an extended period e.g. up to 2½ years after the patient has ceased to take resveratrol.

The invention further provides a method of treating or preventing non-alcoholic fatty liver disease, which comprises administering to a patient suffering from, or at risk of said disease micronized trans-resveratrol in 50-200 mg unit dosage form as a single unit dose daily.

The invention yet further provides a method for the prevention, treatment or reversal of non-alcoholic hepatic steatosis which comprises administering to a patient suffering from, or at risk of said disease micronized trans-resveratrol in 50-200 mg unit dosage form as a single unit dose daily.

The invention yet further provides trans-resveratrol in unit dosage form for administration as a daily dose of 50-200 mg dose to human patients over a period sufficient to induce reversal of non-alcoholic hepatic steatosis persisting after the end of the treatment period. Inducement of steatosis reversal may require a period of one month or more, e.g. more than 2 months and e.g. a period of 6 months, and the resulting reversal may endure after the period of administration for a period of 6 months or more e.g. 2½ years or more.

Alternatively, the invention provides a method of reversing non-alcoholic hepatic steatosis which comprises administering to a human patient exhibiting said steatosis trans-resveratrol in unit dosage form to give a dosage of 50-200 mg unit dosage form daily over a period of more than one month for reversal of non-alcoholic hepatic steatosis persisting after the end of the treatment period.

Evidence for its effectiveness is provided in a study based on two patient groups. A total of 44 patients (28 men and 16 women) were randomly assigned to two groups and were given a single dose of 50 mg resveratrol micronized formulation (n=22) and a single dose of 200 mg resveratrol micronized formulation (n=22) correspondingly on a daily basis. The study continued for 6 moths, after which patients were followed up for a further six months from the end of the study and some patients were followed up at 2 years 6 months from the end of the study.

Quantitative fat measurement, with ultrasound on the liver and kidney, were carried out. There was an initial measurement (time 1) and one after six months (time 2). The study shows the effects of resveratrol micronized formulation in reducing the liver fat, decreasing hepatic enzymes, Serum Glutamate Pyruvic Transaminase (SGPT) and Gamma-Glutamyl Transpeptidase (g-GT) and decreasing insulin resistance. At the end of the study the statistical analysis showed a strongly statistically significant reduction on the liver fat as evidenced by ultrasound measurements of the patients from group A and group B during the study, 0 month (start of the study), 6 months (end of the study), and measurements 6 months from the end of the study and 2.5 years from the end of the study. As will be apparent, the results were highly positive, see the difference (Liver value Kidney Value) which is decreased during the time, even 2.5 years after the end of the study. These data demonstrate that use of resveratrol micronized formulation improves features of NAFLD, prevents liver damage and that resveratrol micronized formulation can be a new treatment method for NAFLD. No adverse reactions (side effects) were noted during the course of the study.

DETAILED DESCRIPTION OF THE INVENTION

The polyphenol resveratrol (RSV) is a stilbenoid and a phytoalexin of the formula below:

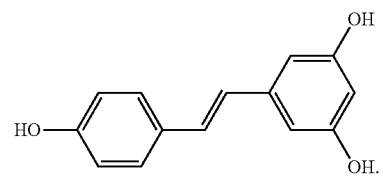 [SMILES: Oc1ccc(/C=C/c2cc(O)cc(O)c2)cc1]

It is produced by several plants in response to injury or when the plant is under attack by pathogens such as bacteria or fungi (Frémont L: Biological effects of resveratrol, *Life Sci.*, 14; 66(8):663-73, 2000). It is found in very low concentrations, in red grapes and in other plants.

WO 2010/100197 (Sergides et al., Agetis Supplements) discloses encapsulated compositions comprising micronized trans-resveratrol and one or more dry pharmaceutically acceptable excipient(s), which are suitable for use as dietary supplements. The term "micronized" refers to particles with a diameter within the micron range. Methods of producing micronized particles are well known in the art, and include friction-based techniques, such as milling and grinding, and supercritical fluid-based techniques, such as the supercritical anti-solvent (SAS) techniques and the rapid expansion of supercritical solutions (RESS) method. Preferably least 90% of the micronized trans-resveratrol particles have a diameter of less than 25 µm. In a preferred embodiment, at least 50% of the micronized trans-resveratrol particles have a diameter of less than 5 µm, and more preferably at least 10% of the micronized trans-resveratrol particles have a diameter of less than 2 µm. Particle size distribution can be determined by laser diffraction methods using a laser diffraction particle size analyser. It is advantageous to pass the mixture of micronized trans-resveratrol and one or more pharmaceutically acceptable excipients through a sieve (for example, a 100 μm sieve) to ensure that no particles with a diameter greater than the desired size, i.e., greater than the sieve pore size, are retained in the product. dry pharmaceutically acceptable excipients suitable for stabilising trans-resveratrol are selected from one or more of soybean powder, starch, colloidal silicon dioxide, microcrystalline cellulose and sodium starch glycolate. In addition, lactose is also suitable for use in the composition and acts as a filler. The micronization of resveratrol increases the particle surface area and enables greater interaction with the excipient molecules, thus increasing stabilisation. The micronization process is also beneficial since increasing the surface area of trans-resveratrol particles increases solubility, absorption and bioavailability for increased efficacy compared to other formulations of resveratrol which are typically of particle size about 0.2 mm. Encapsulation e.g. in gelatine to maintain dryness and reduce isomerisation to the less-active cis-form during storage is desirable.

Evelor 50 mg capsules (Agetis) for oral administration contain micronized trans-resveratrol together with lactose monohydrate, soybean powder, pre-gelatinized maize starch, magnesium stearate, silicon dioxide, gelatin, titanium dioxide (E171), carmoisine (E122), patent blue (E131). Similar Evelor Forte 100 mg capsules contain micronized trans-resveratrol together with lactose monohydrate, croscarmellose sodium, microcrystalline cellulose, hydroxypropyl methylcellulose, magnesium stearate, polyvinyl alcohol, titanium dioxide (E171), talc, polyethylene glycol, lecithin, red iron oxide (E172). Evelor-H capsules contain 200 mg of trans-resveratrol and the same other ingredients as Evelor Forte capsules.

In this study. 50 mg or 200 mg RSV daily were supplemented to the standard treatment of 44 patients with NAFLD for a period of 6 months and the therapeutic efficacy of RSV was investigated. All patients who participated in this process were volunteers and they have provided written consents as well filled out all the required documents. The patients were selected after they were firstly diagnosed with non-alcoholic fatty liver disease. The primary inclusion criterion was evidence of tatty liver on ultrasonography (LS), which is the most commonly, used imaging technique with remarkable sensitivity. The US findings in non-alcoholic fatty liver disease are:

1) diffuse enhancement of near field echo in the hepatic region (stronger than in the kidney and in the spleen region) and gradual attenuation of the tar field echo, 2) unclear display of intra-hepatic lacuna structure.

3) mild to moderate hepatomegaly with a round and blunt border and 4) unclear display of envelop of right liver lobe and diaphragm (Zeng M D, Fang, Lu L G, et al. Guidelines for the diagnosis and treatment of non-alcoholic fatty liver diseases, *J Dig Dis* 9:113-6, 2008).

The study excluded patients with one or more of the following features:
  i) any known causes of steatosis.
  ii) cirrhosis,
  iii) malignant tumour or any other diseases which significantly decrease the patient's lifespan,
  iv) symptoms of heart failure or acute coronary syndrome,
  v) chronic kidney disease,
  vi) psychiatric disorders,
  vii) participating in other similar studies or who participated in other studies which were completed in the last 6 months and
  viii) using food supplements, as they would have to stop the supplement and wait for two weeks before participating in the study.

Equipment Used

A GE Log IQ5 expert Ultrasound Machine equipped with Ultrasound Transducer Probe (GE 3.5C model 2050357) The equipment can measure the Echo Level (EL) at specific areas and depths. EL measures the mean intensity of pixels within a user defined area (region of interest). Raw data provides the average sum (intensity per pixel)/pixels. The ultrasound depicts on screen the area (in $cm^2$), mean (intensity dB) and standard deviation (dispersion) Phantom Model 040GSE (CIRS-Multi Purpose, Multi Tissue u/s Phantom) to calibrate the Log IQ. The specific phantom simulates the human liver and kidney organs and serves for calibration.

Method of Calculation

Regarding the parameters "liver/kidney value" and "liver/kidney depth" we used the same methodology used by Ming-Feng Xia et al., Standardized Ultrasound Hepatic/Renal Ratio and Hepatic Attenuation Rate to Quantify Liver Fat Content: An Improvement Method 10.1038/oby.2011.302.

Ultrasound studies were performed by an experienced radiologist who was unaware of the patient's clinical details and laboratory findings. All the instrument settings, including gain and depth were fixed for each measurement. For assessment of ultrasound hepatic/renal echo value, ultrasound images with both liver and right kidney clearly visualized were obtained in the sagittal liver/right kidney view in the lateral position. A region of interest (ROI) was carefully selected excluding blood vessels, bile ducts and other focal hypoechoic or hyperechoic regions. Another ROI was identified in the right renal cortex with no large vessels, renal sinus or medulla. To avoid the interference of depth-depended echo-intensity attenuation and the borderline echo distorting effects, the boundary between liver and right kidney area should be placed near the center of the image, and the liver and right kidney ROIs were selected at the same depth of the ultrasound images. The gray scale mean value of the pixels within the two ROIs was used as measurement of echo intensity then we subtracted the average hepatic gray scale by the average renal cortex gray scale to calculate the US hepatic/renal value.

Standardization of ultrasound quantitative parameters was performed using an abdominal phantom.

Attenuation measurements were taken at 2 depths, at the Regions of Interest (ROI) xxcm (liver) and yycm (kidney). Attenuation was calculated by subtracting the EL (liver)−EL (kidney)=Hepato-Renal Index Difference. EL is measured in dB and is linear to the intensity, hence can apply linear regression to compute normalized values (Hilde L von, Roald F H, Else M L et al: Quantitative measurement of ultrasound attenuation and Hepato-Renal Index in Non-Alcoholic Fatty Liver Disease, *Med Ultrason, Vol.* 15, no. 1, 16-22, 2013).

A. US Hepatic/Renal Echo Value

In sagittal liver/right kidney view, a region of interest (ROI) of 1.5×1.5 cm (1,296 pixels) in the liver parenchyma was selected. The ROI had to be as uniform as possible, excluding blood vessels, bile ducts, and other focal hypo/hyper-echogenicity. Another ROI of 0.5×0.5 cm (144 pixels) was identified in the right renal cortex with no large vessels, renal sinus or medulla. To avoid the interference of depth-depended echo-intensity attenuation and the borderline echo distorting effects, the boundary between liver and right kidney area should be placed near the center of the image, and the liver and right kidney ROIs were selected at the same depth of the ultrasound images. The gray scale mean value of the pixels within the two ROIs was used as measurement of echo intensity. Then we subtracted the average hepatic gray scale by the average renal cortex gray scale to calculate the US hepatic/renal value.

B. US Hepatic Echo-Intensity Attenuation Rate

In right intercostals view at anterior axilla line, a tangent line of the sector ultrasound image was drawn and the ultrasound wave transmission line was determined, starting from the point of tangency and perpendicular to the tangent line. Two ROIs of 1.5×1.5 cm (1,296 pixels) were selected in liver homogeneous regions along the ultrasound transmission line near the liver anterior margin (depth 4-6 cm) and the liver posterior margin, respectively. The linear distance between the two ROIs was also measured the echo intensity of ultrasound wave was attenuated exponentially, shown as the following equation:

$$A_d = A_0 \times e^{-a f d} \quad (1)$$

where $A_0$ and $A_d$ are ultrasound echo intensity at the sound source and the liver parenchyma at a specific depth, respectively; a is the attenuation coefficient of the liver parenchyma; f is the frequency of the ultrasound detector; d is the depth of ROI. The ratio of the average echo intensity in the liver near-field ROI to liver far-field ROI was then calculated based on equation (1):

$$A_n/A_f = e^{a f (df - dn)} \quad (2)$$

where $A_n$ and $A_f$ are average ultrasound echo intensity in the near-field ROI and the far-field ROI, respectively; a and f have been defined in equation (1); $d_n$ and $d_f$ are the depth of liver near-field and far-field ROIs. Then the formula for ultrasound hepatic echo-intensity attenuation rate was deduced from equation (2):

$$a = (\ln A_n - \ln A_f)/(\Delta d \cdot f) \quad (3)$$

where $\Delta d$ is the distance between the near-field and far-field ROIs, and other parameters are defined in equation (2).

C. Standardization of Ultrasound Quantitative Parameters

To standardize the measured values of US H/R value and hepatic echo-intensity attenuation rate among different ultrasound machines, a 3D abdominal phantom, containing mimic abdominal organs, was used for standardization in this research.

Treatment Method.

Participants underwent clinical examination, electrocardiogram and abdominal ultrasound. Also, blood tests were carried out and the following parameters were measured: serum glutamic pyruvic transaminase (SGPT), serum glutamic oxaloacetic transaminase (SGOT), Alkaline phosphatase (ALP), gamma-glutamyl transpeptidase (gGT), glucose, total cholesterol levels, high-density lipoprotein (HDL), low-density lipoprotein (LDL), triglycerides (TG), insulin, insulin resistance, liver value, liver depth, kidney value, kidney depth and difference liver-kidney values.

Then, the patients were divided into two groups (randomly assigned) according to the treatment given to them. 22 patients were given treatment 50 mg RSV micronized formulation, Evelor capsules once daily, (Group A) and 22 patients were given treatment 200 mg RSV micronized formulation, Evelor capsules, once daily, (Group B). The observation period lasted for 6 months. There was a clinical examination, blood tests and an abdominal ultrasound at the beginning of the study (time 1) and in 6 months (time 2). All patients were on low fat diet and they were being followed up by nutritionist.

The results obtained by the study were used to examine the following parameters:
 i) the count of hepatic enzymes,
 ii) the insulin resistance and
 iii) the liver fat.

Statistical Analysis

Two-way ANOVA with interaction (time and group) was used to test whether there are differences among dose levels, time levels and possible interaction among them. However, no significant interactions were discovered and standard two-way ANOVA was used without interactions. Moreover, an independent t-test was conducted to examine whether there were any differences between the values of physiological parameters at the beginning and the end of the study. A p-value<0.001 was considered to indicate a strongly statistically significant difference. The statistical program used was R 3.2.1.

Results

A total of 44 patients participated in the study, 28 men and 16 women. The patients were divided into groups, according to the treatment given to them, 22 in each group.

Group A was treated with Resveratrol micronized formulation 50 mg

Group B was treated with Resveratrol micronized formulation 200 mg

Table I contains summary statistics for all participants in the study for the main demographic variables and the Table II shows cross classification of the participants by gender and by treatment.

TABLE I

Main demographic variables

| | mean | SD | Median | Minimum | Maximum |
|---|---|---|---|---|---|
| AGE (YEARS) | 54.16 | 9.92 | 55 | 29 | 70 |
| WEIGHT (kg) At time 1 | 84.55 | 11.42 | 83.30 | 58 | 105 |
| Weight(kg) At time 2 | 82.33 | 11.73 | 80 | 57 | 103 |
| Height (cm) | 170 | 7 | 170 | 155 | 183 |
| BMI(kg/cm$^2$) At time 1 | 27.01 | 3.02 | 28 | 20 | 31 |
| BMI(kg/cm$^2$) At time 2 | 27.93 | 3.35 | 28.50 | 21 | 35 |

TABLE II

Classification of the participants by gender and by treatment

| | Dose | |
|---|---|---|
| Sex | 50 mg RSV | 200 mg RSV |
| Male (M) | 12 | 16 |
| Female (F) | 10 | 6 |

Table III contains the mean values of all the variables in the beginning (time 1) and at the end (time 2) of the study and the results of comparisons among different time points for those participants in the 50 mg group. The following conclusions were obtained:

There are strongly statistically significant differences among liver values, between time 1 and time 2. The liver values in time 2 decrease.

There are strongly statistically significant differences among kidney values between time 1 and time 2. The kidney values in time 2 decrease.

There are significant differences among insulin resistance between time 1 and time 2.

TABLE III

Statistical Comparisons based only on 50 mg Dose across Time

|  | Mean at time 1 | Mean at time 2 | t-test (p-value) |
|---|---|---|---|
| SGPT | 36.09 | 37.24 | 0.871 |
| SGOT | 24.95 | 26.33 | 0.603 |
| ALP | 63.63 | 59.23 | 0.593 |
| gGT | 30.95 | 27.00 | 0.770 |
| GLU | 105.95 | 96.57 | 0.122 |
| CH | 194.50 | 185.67 | 0.656 |
| HDL | 48.60 | 47.67 | 0.905 |
| LDL | 119.45 | 116.19 | 0.932 |
| TG | 132.50 | 109.76 | 0.301 |
| Insulin | 13.58 | 12.69 | 0.206 |
| Insulin Resistance | 1405.81 | 1226.04 | 0.135 |
| Liver Value | 55.20 | 45.42 | <0.001 |
| Liver Depth | 5.60 | 5.79 | 0.034 |
| Kidney value | 32.49 | 28.42 | <0.001 |
| Kidney depth | 7.06 | 7.30 | 0.008 |
| Difference L − K value | 22.71 | 17.00 | 0.170 |

Table IV contains the mean values of all the variables in the beginning (time 1) and at the end (time2) of the study and the results of comparisons among different time points for those participants in the 200 mg group. The following conclusions were obtained:

There are strongly statistically significant differences among liver values between time 1 and time 2. The liver values in time 2 decrease There are strongly statistically significant differences among kidney values between time 1 and time 2. The kidney values in time 2 decrease.

There are significant differences among insulin resistance between time 1 and time 2.

TABLE IV

Statistical Comparisons based only on 200 mg Dose across Time

|  | Mean at time 1 | Mean at time 2 | t-test (p-value) |
|---|---|---|---|
| SGPT | 47.05 | 41.70 | 0.631 |
| SGOT | 32.81 | 30.90 | 0.887 |
| ALP | 74.50 | 71.20 | 0.804 |
| gGT | 29.20 | 25.35 | 0.434 |
| GLU | 121.18 | 112.50 | 0.786 |
| CH | 194.27 | 181.15 | 0.258 |
| HDL | 41.14 | 41.70 | 0.832 |
| LDL | 118.75 | 105.95 | 0.408 |
| TG | 205.13 | 167.80 | 0.465 |
| Insulin | 12.62 | 13.01 | 0.091 |
| Insulin Resistance | 1541.04 | 1489.52 | 0.151 |
| Liver Value | 58.77 | 43.33 | <0.001 |
| Liver Depth | 5.20 | 5.63 | 0.792 |
| Kidney value | 32.30 | 25.21 | <0.001 |
| Kidney depth | 7.04 | 7.26 | 0.795 |
| Difference L − K value | 26.46 | 18.115 | 0.795 |

Table V contains the comparisons among groups and different time points for all participants in the study.

A two-way ANOVA model is used with interaction to test whether there are differences among dose levels, time levels and possible interaction among them. The following conclusions were obtained:

There are strongly statistically significant differences between liver values and kidney values across the time. Both of these measurements decrease (time 2).

The Difference Liver-Kidney decrease as time progress.

There are significant differences between the two dose levels for ALP and TG.

There are significant differences between the dose levels for SGOT, Glucose and HDL.

There is no interaction between dose and time for all variables considered.

TABLE V

Statistical Comparisons based on different Doses and across Time

|  | Time Effect (p-value) | Dose Effect (p-value) | Interaction between Time and Dose (p-value) |
|---|---|---|---|
| SGPT | 0.842 | 0.052 | 0.576 |
| SGOT | 0.991 | 0.022 | 0.686 |
| ALP | 0.563 | 0.002 | 0.883 |
| gGT | 0.567 | 0.377 | 0.798 |
| GLU | 0.336 | 0.005 | 0.963 |
| CH | 0.215 | 0.563 | 0.863 |
| HDL | 0.983 | 0.004 | 0.764 |
| LDL | 0.479 | 0.190 | 0.697 |
| TG | 0.183 | 0.002 | 0.898 |
| Insulin | 0.027 | 0.782 | 0.887 |
| Insulin Resistance | 0.021 | 0.179 | 0.914 |
| Liver Value | <0.001 | 0.621 | 0.383 |
| Liver Depth | 0.136 | 0.821 | 0.376 |
| Kidney value | <0.001 | 0.287 | 0.778 |
| Kidney depth | 0.051 | 0.330 | 0.350 |
| Difference L − K value | 0.001 | 0.681 | 0.424 |

Based on the fact that there is no interaction between dose and time for all variable considered, a two-way ANOVA model is also implemented but without interaction.

Table VI contains the comparisons among groups and different time points for all participants in the study.

The results show the same conclusions as in the case of a model which includes interactions. There are strongly statistically significant differences between liver values and kidney values across the time. Both of these measurements decrease (time 2).

The Difference Liver-Kidney decrease as time progress.

There are significant differences between the two dose levels for ALP and TG.

There are significant differences between the dose levels for SGOT, Glucose and HDL.

TABLE VI

Statistical Comparisons based on different Doses and across Time

|  | Time Effect (p-value) | Dose Effect (p-value) |
|---|---|---|
| SGPT | 0.841 | 0.051 |
| SGOT | 0.991 | 0.022 |
| ALP | 0.556 | 0.002 |
| gGT | 0.563 | 0.374 |
| GLU | 0.330 | 0.004 |
| CH | 0.211 | 0.460 |
| HDL | 0.983 | 0.004 |
| LDL | 0.475 | 0.187 |
| TG | 0.179 | 0.002 |
| Insulin | 0.025 | 0.781 |
| Insulin Resistance | 0.020 | 0.176 |
| Liver Value | <0.001 | 0.621 |
| Liver Depth | 0.136 | 0.821 |
| Kidney value | <0.001 | 0.284 |
| Kidney depth | 0.051 | 0.331 |
| Difference L − K value | 0.001 | 0.681 |

Tables showing ultrasound measurements of the patients from group A and group B during the study, 0 month, 6 months, and measurements after the study, 6 months and 2.5 years. After the end of the trial the supervisor nurse, Mrs. Antria Aristotelous, confirmed that only a single patient of group A No. 8. M. O took RSV for few months following the trial and then discontinued it, and that the remaining four patients discontinued it immediately. The results given below therefore indicate not only near-term but also lasting benefits in taking resveratrol at relatively low dosages for patients suffering from NAFLD.

Tables VII-IX: Patient's from Group (A) Treated with 50 mg Resveratrol

TABLE VII

| Serial Number. Initial of Surname and Name. | First (1st) ultrasound date. 0 month | Liver Value. | Liver Depth. | Kidney Value. | Kidney Depth. | 2.5 cm −3 db. | 2.5 cm +6 db. | 12 cm −3 db. | 12 cm +6 db. | Difference (Liver Value − Kidney Value) |
|---|---|---|---|---|---|---|---|---|---|---|
| 4. Π. X | 30 May 2013 | 55.9 | 7.0 | 32.6 | 8.2 | 25.7 | 57.6 | 14.1 | 43.3 | 23.3 |
| 6. M. I | 11 Mar. 2014 | 96.1 | 4.0 | 52.4 | 5.9 | 59.7 | 97.0 | 39.5 | 68.1 | 43.7 |
| 8. M. O | 17 Jul. 2013 | 41.3 | 3.7 | 7.0 | 5.2 | 40.0 | 73.0 | 28.8 | 49.4 | 34.3 |
| 14. Λ. O | 13 Oct. 2013 | 45.0 | 3.8 | 30.4 | 5.6 | 28.6 | 55.9 | 16.1 | 33.8 | 14.6 |
| 15. A. I | 22 Oct. 2013 | 67.9 | 5.5 | 35.0 | 6.6 | 37.5 | 64.5 | 22.3 | 43.3 | 32.9 |
| 21. A. M | 25 Jan. 2014 | 45.4 | 5.9 | 25.3 | 7.4 | 30.4 | 54.2 | 16.4 | 42.6 | 20.1 |

TABLE VIII

| Serial Number. Initial of Surname and Name. | Second (2nd) ultrasound date. 6 months | Liver Value. | Liver Depth. | Kidney Value. | Kidney Depth. | 2.5 cm −3 db. | 2.5 cm +6 db. | 12 cm −3 db. | 12 cm +6 db. | Difference (Liver Value − Kidney Value) |
|---|---|---|---|---|---|---|---|---|---|---|
| 4. Π. X | 20 Nov. 2013 | 49.8 | 6.2 | 30.8 | 7.1 | 28.4 | 45.6 | 10.0 | 35.9 | 19 |
| 6. M. I | 2 Sep. 2014 | 45.0 | 7.2 | 26.5 | 10.0 | 23.1 | 54.3 | 10.4 | 39.3 | 18.5 |
| 8. M. O | 15 Jan. 2014 | 41.9 | 4.3 | 21.0 | 5.4 | 25.5 | 61.9 | 23.0 | 48.8 | 20.9 |
| 14. Λ. O | 8 Apr. 2014 | 42.0 | 4.8 | 29.2 | 5.9 | 25.8 | 40.6 | 7.3 | 40.0 | 12.8 |
| 15. A. I | 18 Apr. 2014 | 55.9 | 5.1 | 26.4 | 5.9 | 23.1 | 43.5 | 9.6 | 35.9 | 29.5 |
| 21. A. M | 17 Jun. 2014 | 31.9 | 4.9 | 20.1 | 6.6 | 30.2 | 54.9 | 9.4 | 34.2 | 11.8 |

TABLE IX

| Serial Number. Initial of Surname and Name. | Third (3rd) ultrasound date. (6 months after the end of the study) | Liver Value. | Liver Depth. | Kidney Value. | Kidney Depth. | 2.5 cm −3 db. | 2.5 cm +6 db. | 12 cm −3 db. | 12 cm +6 db | Difference (Liver Value − Kidney Value) |
|---|---|---|---|---|---|---|---|---|---|---|
| 4. Π. X | 5 May 2014 | 85.2 | 2.1 | 67.6 | 3.5 | 66.8 | 99.5 | 60.9 | 85.1 | 17.6 |
| 6. M. I | 8 Mar. 2015 | 57.5 | 1.8 | 48.1 | 2.9 | 47.9 | 84.7 | 44.0 | 85.2 | 9.4 |
| 8. M. O | 13 Jun. 2014 | 97.8 | 6.8 | 81.1 | 6.2 | 98.7 | 146.2 | 52.5 | 82.4 | 16.7 |
| 14. Λ. O | 10 Oct. 2014 | 70.3 | 2.5 | 60.0 | 4.5 | 69.3 | 105.8 | 58.1 | 87.7 | 10.3 |
| 15. A. I | 13 Oct. 2014 | 88.9 | 2.6 | 64.5 | 3.7 | 46.2 | 101.6 | 51.0 | 86.7 | 24.4 |
| 21. A. M | 15 Dec. 2014 | 58.9 | 2.9 | 57.3 | 4.0 | 68.0 | 106.3 | 53.7 | 89.3 | 1.6 |

TABLES X-XII: Patient's from Group (B) Treated with 200 mg Resveratrol

TABLE X

| Serial Number. Initial of Surname and Name. | First (1st) ultrasound date. 0 month | Liver Value. | Liver Depth. | Kidney Value. | Kidney Depth. | 2.5 cm −3 db. | 2.5 cm +6 db. | 12 cm −3 db. | 12 cm +6 db. | Difference (Liver Value − Kidney Value) |
|---|---|---|---|---|---|---|---|---|---|---|
| 4. K. N | 7 May 2013 | 34.7 | 6.0 | 14.2 | 8.3 | 27.5 | 25.6 | 10.7 | 6.9 | 20.5 |
| 6. A. A | 14 Apr. 2013 | 69.6 | 6.0 | 28.6 | 5.6 | 46.8 | 81.6 | 31.0 | 46.7 | 41 |
| 7. Π. A | 10 Jun. 2013 | 52.1 | 8.2 | 33.3 | 9.8 | 41.7 | 72.9 | 21.8 | 52.9 | 18.8 |
| 9. Λ. E | 28 Jun. 2013 | 60.4 | 2.9 | 32.2 | 3.6 | 32.8 | 68.0 | 18.1 | 15.0 | 28.2 |
| 11. Σ. O | 11 Aug. 2013 | 62.0 | 5.0 | 26.5 | 5.5 | 29.7 | 59.7 | 22.6 | 31.6 | 35.5 |
| 15. M. X | 12 Dec. 2013 | 55.9 | 5.9 | 23.6 | 8.0 | 33.8 | 71.1 | 25.3 | 45.6 | 32.3 |
| 18. A. Π | 25 Jan. 2014 | 86.8 | 2.2 | 39.5 | 3.8 | 43.7 | 79.6 | 20.8 | 41.1 | 47.3 |
| 19. M. M | 28 Jan. 2014 | 46.8 | 5.6 | 22.7 | 7.3 | 32.0 | 68.8 | 11.6 | 39.7 | 24.1 |

TABLE XI

| Serial Number. Initial of Surname and Name. | Second (2nd) ultrasound date. 6 months | Liver Value. | Liver Depth. | Kidney Value. | Kidney Depth. | 2.5 cm −3 db. | 2.5 cm +6 db. | 12 cm −3 db. | 12 cm +6 db. | Difference (Liver Value − Kidney Value) |
|---|---|---|---|---|---|---|---|---|---|---|
| 4. K. N | 27 Nov. 2013 | 49.8 | 6.9 | 42.4 | 8.3 | 30.4 | 50.3 | 8.7 | 39.5 | 7.4 |
| 6. A. A | 27 Oct. 2013 | 50.5 | 5.6 | 17.0 | 5.5 | 21.4 | 50.7 | 11.5 | 37.3 | 33.5 |
| 7. Π. A | 30 Dec. 2013 | 33.2 | 7.3 | 16.8 | 9.5 | 21.9 | 49.1 | 11.2 | 36.8 | 16.4 |
| 9. Λ. E | 10 Dec. 2013 | 47.8 | 3.6 | 33.0 | 4.4 | 12.3 | 58.6 | 9.5 | 32.9 | 14.8 |
| 11. Σ. O | 2 Feb. 2014 | 46.0 | 7.1 | 22.1 | 8.2 | 26.9 | 34.4 | 9.0 | 33.7 | 23.9 |
| 15. M. X | 17 May 2014 | 50.1 | 5.4 | 31.1 | 7.3 | 31.6 | 65.5 | 20.3 | 49.3 | 19 |
| 18. A. Π | 2 Jul. 2014 | 53.1 | 2.6 | 18.9 | 4.7 | 32.2 | 57.4 | 14.5 | 40.6 | 34.2 |
| 19. M. M | 17 Jul. 2014 | 36.6 | 6.4 | 14.4 | 7.4 | 29.7 | 58.9 | 11.0 | 37.9 | 22.2 |

TABLE XII

| Serial Number. Initial of Surname and Name. | Third (3rd) ultrasound date. (6 months after the end of the study) | Liver Value. | Liver Depth. | Kidney Value. | Kidney Depth. | 2.5 cm −3 db. | 2.5 cm +6 db. | 12 cm −3 db. | 12 cm +6 db | Difference (Liver Value − Kidney Value) |
|---|---|---|---|---|---|---|---|---|---|---|
| 4. K. N | 27 May 2014 | 81.3 | 7.7 | 75.3 | 9.7 | 68.6 | 111.5 | 57.6 | 87.8 | 6 |
| 6. A. A | 27 Apr. 2014 | 57.2 | 4.2 | 40.4 | 5.7 | 42.5 | 60.0 | 80.0 | 112.4 | 16.8 |
| 7. Π. A | 18 May 2014 | 74.9 | 9.9 | 61.7 | 9.8 | 39.0 | 120.3 | 67.3 | 87.6 | 13.2 |
| 9. Λ. E | 18 May 2014 | 61.9 | 1.7 | 53.0 | 3.9 | 67.8 | 111.1 | 66.6 | 106.6 | 8.9 |
| 11. Σ. O | 27 Oct. 2014 | 77.3 | 5.0 | 55.2 | 5.4 | 67.5 | 106.4 | 86.7 | 54.6 | 22.1 |
| 15. M. X | 28 Nov. 2014 | 94.3 | 6.5 | 84.3 | 7.9 | 58.8 | 108.8 | 58.8 | 95.0 | 10 |
| 18. A. Π | 2 Jan. 2015 | 74.2 | 1.9 | 55.9 | 3.3 | 58.0 | 85.8 | 53.4 | 89.1 | 18.3 |
| 19. M. M | 17 Jan. 2015 | 85.2 | 6.2 | 71.5 | 8.1 | 63.2 | 89.6 | 54.3 | 82.4 | 13.7 |

TABLE XIII

Patient's from Group (A) who were treated during the study with 50 mg Resveratrol

| Serial Number. Initial of Surname and Name. | Forth (4rth) ultrasound after 2.5 years. From the end of the study. | Liver Value. | Liver Depth. | Kidney Value. | Kidney Depth. | 2.5 cm −3 db. | 2.5 cm +6 db. | 12 cm −3 db. | 12 cm +6 db. | Difference (Liver Value − Kidney Value) |
|---|---|---|---|---|---|---|---|---|---|---|
| 8. M.O | 11 Aug. 2017 | 85.0 | 4.6 | 75.2 | 4.7 | 76.2 | 117.0 | 47.7 | 84.0 | 9.8 |
| 15. A. I | 11 Aug. 2017 | 80.5 | 4.0 | 75.0 | 4.8 | 69.5 | 109.4 | 55.9 | 93.5 | 5.5 |

TABLE XIV

Patient's from Group (B) who were treated during the study with 200 mg Resveratrol

| Serial Number. Initial of Surname and Name. | Forth (4rth) ultrasound after 2.5 years. From the end of the study. | Liver Value. | Liver Depth. | Kidney Value. | Kidney Depth. | 2.5 cm −3 db. | 2.5 cm +6 db. | 12 cm −3 db. | 12 cm +6 db. | Difference (Liver Value − Kidney Value) |
|---|---|---|---|---|---|---|---|---|---|---|
| 7. Π. A | 11 Aug. 2017 | 60.1 | 10.0 | 42.8 | 10.4 | 50.4 | 89.0 | 40.7 | 81.8 | 17.3 |
| 11. Σ. O | 8 Aug. 2017 | 39.1 | 7.1 | 31.2 | 8.7 | 20.0 | 30.0 | 28.7 | 23.8 | 7.9 |
| 15. M. X | 8 Aug. 2017 | 46.0 | 6.0 | 41.0 | 6.1 | 26.5 | 26.3 | 24.6 | 21.2 | 5 |

The invention claimed is:

1. A method of treating a human patient exhibiting non-alcoholic hepatic steatosis associated with fatty liver disease by administering over a period of at least 6 months a micronized trans-resveratrol composition to give a daily dosage of 50-200 mg, said composition consisting essentially of the micronized trans-resveratrol, one or more dry pharmaceutically acceptable excipients selected from soybean powder, starch, colloidal silicon dioxide, microcrystalline cellulose and sodium starch glycolate and also comprising lactose which acts as a filler, at least 90% of the micronized trans-resveratrol particles having a diameter of less than 25 μm, at least 50% of the micronized trans-resveratrol particles having a diameter of less than 5 μm and at least 10% of the micronized trans-resveratrol particles having a diameter of less than 2 μm, said composition being in unit dosage form in the form of capsules, wherein administration reverses the non-alcoholic hepatic steatosis giving a reduction in liver fat observable by ultrasound measurements and said reversal persists for at least 6 months after the end of the treatment period.

2. The method of claim 1, wherein it has been prior ascertained that the patient exhibits evidence of fatty liver on ultrasonography.

3. The method of claim 2, wherein it has been prior ascertained that the patient exhibits one or more of:
   (a) diffuse enhancement of near field echo in the hepatic region (stronger than in the kidney and in the spleen region) and gradual attenuation of the far field echo,
   (b) unclear display of intra-hepatic lacuna structure,
   (c) mild to moderate hepatomegaly with a round and blunt border and/or
   (d) unclear display of envelope of right liver lobe and diaphragm.

4. The method of claim 1, wherein the period of persistence after the end of the treatment period is at least 2.5 years.

5. A method of treating a human patient exhibiting non-alcoholic hepatic steatosis associated with fatty liver disease by administering over a period of at least 6 months a micronized trans-resveratrol composition to give a daily dosage of 50-200 mg,
   said composition consisting essentially of the micronized trans-resveratrol, one or more dry pharmaceutically acceptable excipients and a filler,
   at least 90% of the micronized trans-resveratrol particles having a diameter of less than 25 µm, at least 50% of the micronized trans-resveratrol particles having a diameter of less than 5 µm and at least 10% of the micronized trans-resveratrol particles having a diameter of less than 2 µm,
   said composition being in unit dosage form in the form of capsules,
   wherein administration reverses the non-alcoholic hepatic steatosis giving a reduction in liver fat observable by ultrasound measurements and said reversal persists for at least 6 months after the end of the treatment period.

* * * * *